United States Patent [19]

Takami et al.

[11] Patent Number: 4,888,289

[45] Date of Patent: Dec. 19, 1989

[54] REAGENT FOR DETERMINING CREATINE KINASE

[75] Inventors: Tetuji Takami; Hiroyki Tsubota; Hisashi Ochi, all of Chiba, Japan

[73] Assignees: Iatron Laboratories, Inc., Tokyo; Unitaka Ltd., Hyogo, both of Japan

[21] Appl. No.: 923,671

[22] Filed: Oct. 27, 1986

[30] Foreign Application Priority Data

Nov. 1, 1985 [JP] Japan .................................. 60-244188

[51] Int. Cl.$^4$ .......................... C12Q 1/48; C12Q 1/50; C12Q 1/32
[52] U.S. Cl. ......................................... 435/15; 435/14; 435/17; 435/26; 435/188; 435/810
[58] Field of Search ...................... 435/14, 17, 15, 188, 435/26, 810; 436/18

[56] References Cited

U.S. PATENT DOCUMENTS

| | | | |
|---|---|---|---|
| 4,012,286 | 3/1977 | Sanderson et al. | 435/15 |
| 4,118,279 | 10/1978 | Determan et al. | 435/188 |
| 4,235,961 | 11/1980 | Lundin | 435/810 |
| 4,438,199 | 3/1984 | Miwa et al. | 435/810 |
| 4,740,458 | 4/1988 | Kondo et al. | 435/17 |

OTHER PUBLICATIONS

Sandifort, C.R.J., Clinical Chemistry, 23, p. 2169, (1977).

Nealon, D. A. et al., Clinical Chemistry, 27, pp. 402-404, (1981).

Szasz, Gabor et al, Clinical Chemistry, 22, pp. 650-656, (1976).

*Primary Examiner*—Esther M. Kepplinger
*Attorney, Agent, or Firm*—Kane, Dalsimer, Sullivan, Kurucz, Levy, Eisele and Richard

[57] ABSTRACT

A reagent for the determination of creatine kinase is comprised of a reagent group containing N-acetylcysteine and ethylenediaminetetraacetic acid and a reagent group containing magnesium, whereby the stability thereof is acheived.

6 Claims, 3 Drawing Sheets

REAGENT FOR DETERMINING CREATINE KINASE

BACKGROUND OF THE INVENTION

1. Field of the Invention

The present invention relates to a reagent for determining the quantity of creatine kinase (hereafter abbreviated as CK) in living body fluids.

2. Related Art Statement

CK occurs in the systemic muscular tissues and brain of a human body and, in the field of clinical examinations, is one of the important items needed for usual diagnosis of muscular diseases, nervous disorders, central nervous system disorders, mental troubles, heart troubles and the like.

CK is an enzyme that catalyzes reversibly the reaction expression in terms of the following formula 1:

$$CP + ADP \underset{}{\overset{CK}{\rightleftharpoons}} C + ATP \quad (1)$$

wherein CP represents creatine phosphate, C represents creatine, ADP represents adenosine diphosphate, and ATP represents adenosine triphosphate.

Heretofore, various methods for the measurement of CK has been proposed. One type of CK measurement is described as the measurement of activity in the lefthand direction in Formula 1, including (i) the measurement of inorganic phosphoric acid formed by hydrolysis of CP, (ii) the derivation of ADP to reduction type beta-nicotinamide adenine dinucleotide (hereinafter abbreviated as NADH) under the action of pyruvate kinase (hereinafter abbreviated as PK) and lactose dehydrogenase (hereinafer abbreciated as LDH) for the determination of absorption losses, and (iii) the derivation of ADP to pyruvic acid with PK, which is in turn allowed to react with 2,4-dinitrophenylhidrazine to measure the resulting hidrazone. The other type is described as the measurement of activity in the right hand direction in Formula 1, including (i) the reaction of the resulting C with a pigment of colorimetry or fluorometry, (ii) the use of luciferase (see Japanese Patent Laid-Open Specification Nos. 51-41597, 55-120796, 56-26200 and 57-105199), (iii) the use of phosphoglyceric acid kinase (hereinafter abbreviated as PGK) and glyceraldehyde-3-phosphate dehydrogenase (hereinafter abbreviated as GAPDH) (see Japanese Patent Publication No. 59-34119 and Japanese Patent Laid-Open Specification No. 56-155000) and (iv) the use of hexokinase (hereinafter abbreviated as HK) and glucose-6-phosphate dehydrogenase (hereinafter abbreviated as G6PDH). The combined HK/G6PDH method is most frequently used, since it is the most excellent in principle, shows improved sensitivity and reproducibility, and can treat a multiplicity of samples.

Incidentally, since CK is an unstable enzyme, the so-called SH group-containing compound (hereinafter called simply the SH reagent) such as N-acetylcysteine (hereinafter abbreviated as NAC), dithiothreitol, glutathione, mercaptoethanol and the like is ordinarily used as the activator for the purpose of enhancing the activation effect of the activity of CK, when its activity value is measured. Reportedly, particular preference is given to NAC (see J. Clin. Chem. Clin. Biochem Vol. 15, pp. 249~254, 1977). The divalentions most preferably used in the reactions on which CK acts are magnesium ions. It is noted that in this connection that some literature reports that, in the reactions of Formula 1 on which CK acts, the km value of magnesium ions is $Mg^{++} 6 \times 10^{-4} M$ for the left hand direction and $Mg^{++} 6 \times 10^{-3} M$ for the right hand direction (see "Clinical Examinations", Vol. 15, No. 12, pp. 1257, 1971). Thus, in addition to the primary components, NAC and magnesium ions are considered to be the ingredients which are essentially and simultaneously required to preferably effect the reactions on which CK acts.

Heretofore, the reagents for the measurement of CK have had the disadvantages that they are poor in storage stability at room temperature in the state of a solution and, in particular, their service life is very short at room temperature (18°~37° C.). Consequently, it has been found that, since such reagents should be used within a short period of time just after preparation, their use is inefficient. For example, in view of the fact that they should individually be prepared whenever a number of samples are treated over a prolonged period. Alternatively, they are unsuitable for use with an emergency automatic analyzer designed to examine a limited number of unexpected but extremely urgent samples. The incorporation of NAC in particular serves to enhance the activation effect on the activity of CK. Since NAC is a relatively unstable reagent, however, the SH group contained therein is gradually oxidized in the state of solution to such an extent that the sufficient activation effect on the activity of CK is no longer sustained. It is further reported that the decomposed product of NAC tends to inhibit the activity of CK (see CLIN. CHEM. Vol. 22, No. 5, pp. 650~656, 1976). Combined with a reduction in the activation effect, this is greatly responsible for the unstableness of the reagent for CK measurement in the state of a solution.

A concrete phenomenon resulting from the unstableness of NAC occurs noticeably when, for instance, serum dilution testing is carried out. To put it more concretely, there is a gradual decrease in the gradient of the calibration curve obtained from the serum dilution testng with the lapse of days after the preparation of reagents, say, a lowering of sensitivity. Clearly, such a phenomenon poses a grave problem in view of accuracy control in clinical examinations.

It is reported, on the other hand, that NAC is stabilized by a chelating agent such as ethylenediaminetetraacetic acid (hereinafter abbreviated as EDTA), and the resulting NAC is kept stable for about 7 days under storage testing at 25° C. However, even such a treatment results in unavoidable occurrence of a factor inhibiting the activity of CK originating from NAC. In practice, the CK activity value achieved with the use of such a reagent for CK measurement remains constant for about two days, when the prepared reagent is stored at 25° C., but later decreases sharply. That is to say, the conclusion that the effect of EDTA upon the stabilization of NAC does not yet reach any practical level can hardly be avoided.

SUMMARY OF THE INVENTION

As a result of extensive and intensive studies made to provide a solution to the problems as mentioned above, it has been found that the effect of EDTA upon the stabilization of NAC is increasingly enhanced by allowing the magnesium salts needed in the measurement of the activity of CK to be contained in a reagent group different from a reagent group containing NAC and EDTA.

More specifically, the present invention provides a reagent for the determination of creatine kinase, said determination being made on the basis of the following reaction formula 1:

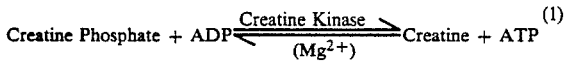

Creatine Phosphate + ADP $\underset{(Mg^{2+})}{\overset{\text{Creatine Kinase}}{\rightleftarrows}}$ Creatine + ATP  (1)

wherein ADP represents adenosine diphosphate, and ATP represents adenosine triphosphate, and using N-acetylcysteine as an activator in the presence of magnesium salts, characterized in that it is comprised of, or prepared from, at least two reagent groups, one being a reagent group containing N-acetylcysteine and ethylenediaminetetraacetic acid and the other being a reagent group containing magnesium.

DESCRIPTION OF THE DRAWINGS

In FIG. 1, a represents a calibration curve using a reagent kit of the present invention immediately after preparation and b a calibration curve using a reagent kit after storage for 28 days from the preparation of the above sample a.

In FIG. 2, c represents a calibration curve using a reagent kit for comparison immediately after preparation where the NAC, EDTA and Mg are contained in one reagent group and d a calibration curve using a reagent kit for comparison after storage for 28 days from the preparation of the above sample c.

In FIG. 3, e represents the stability of NAC in a solution containing the NAC and EDTA, f the stability of NAC in a solution containing the NAC, EDTA and magnesium acetate and g the stability of NAC in a solution of NAC only.

DETAILED DESCRIPTION OF THE INVENTION

Figure 1:
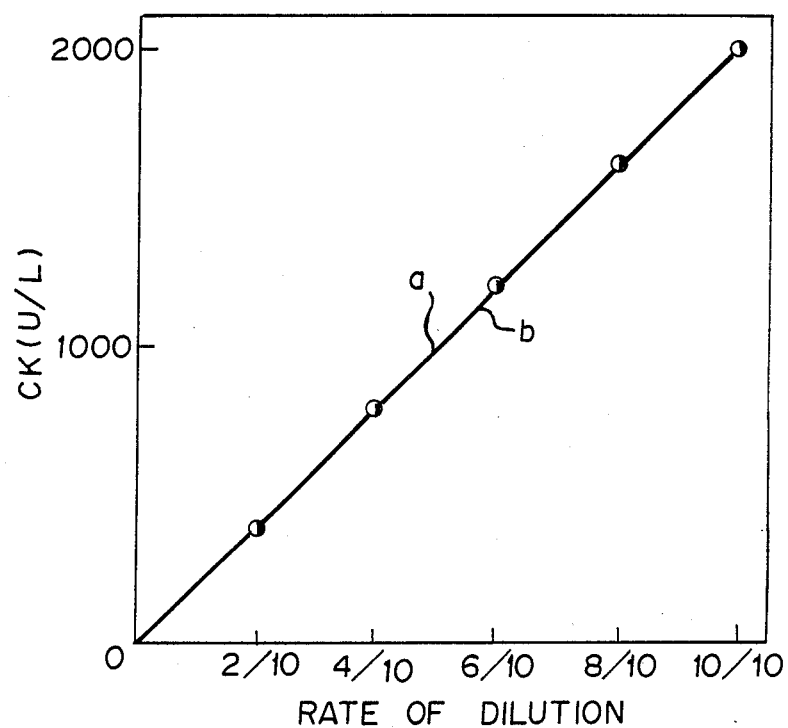
FIG. 1 is a graphical view illustrating the stability of the reagent according to the present invention.

In what follows, the present invention will be explained in further detail.

For a better understanding of the present invention, the concrete reaction systems for the determination of CK will now be described with reference to the following reaction formula 1~3.

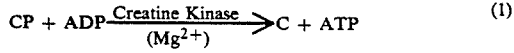

CP + ADP $\underset{(Mg^{2+})}{\overset{\text{Creatine Kinase}}{\longrightarrow}}$ C + ATP  (1)

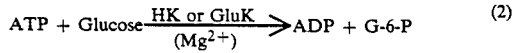

ATP + Glucose $\underset{(Mg^{2+})}{\overset{\text{HK or GluK}}{\longrightarrow}}$ ADP + G-6-P  (2)

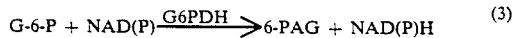

G-6-P + NAD(P) $\overset{\text{G6PDH}}{\longrightarrow}$ 6-PAG + NAD(P)H  (3)

where, of the abbreviations as given above, GluK represents Gluco Kinase, G-6-P represents glucose-6-phosphate, NAD(P) represents beta-nicotinamide adenine dinucleotide (phosphate), NAD(P)H represents reduction type beta-nicotinamide adenine dinucleotide (phosphate), and 6-PGA represents 6-phosphogluconate.

In the reagents used for the determination of the activity of creatine kinase based on the aforesaid reaction systems and containing as the essential components at least CP, ADP, glucose, HP or GluK, NAD(P), G6PDH, magnesium salts, NAC and EDTA, the reagents of the present invention are comprised of, or prepared from, at least two reagent groups, one being a reagent group containing NAC and EDTA and the other being a reagent group containing magnesium salts.

The reagents of the present invention contain, for instance, CP, ADP, glucose, HK or GluK, NAD(P) and G6PDH as the main components taking part in the reactions involved. Usually, they contain NAC as the activator and further includes EDTA and magnesium salts. It is then required that the reagent group containing NAC and EDTA be provided separately from the reagent group containing magnesium salts.

The present invention provides a reagent for the determination of CK which is comprised of, or prepared from, at least two reagent groups, one being a reagent group containing NAC and EDTA which are the additives according to Reaction Formula 1, and the other being a reagent group containing magnesium salts, regardless of the types of Reaction Formulae 2 and 3.

Usually, it is particularly convenient to divide the reagent into such reagent groups in view of the fitness for measuring equipment. In some cases, however, the measuring reagent may be obtained by separately providing or adding other suitable reagent to the reagent groups containing NAC.EDTA and magnesium salts.

The measurements according to Reaction Formulae 1, 2 and 3 may be carried out, while the reagent group containing ADP, glucose, HK or GluK, NAD(P), G6PDH, NAC, EDTA and the like is provided separately from the reagent group containing CP and magnesium salts and the like.

In most cases, it is usual that NAC and EDTA are contained in the first reagent group including the main components required for the reactions, while the magnesium salts are contained together with the substrate for CK in the second reagent group. The activation of CK in a sample under test is effected in the first reaction liquid. Subsequently, with the addition of the substrate in the second reaction liquid, the actual measurement of CK is started.

In the one-liquid batch method wherein the measurement of CK is carried out from the outset in a single-liquid batch, the first and second reaction liquids may be mixed together in a suitable proportion just prior to use. It is in fact impossible to completely free the reagent group containing NAC and EDTA of magnesium ions. However, the presence of a minute amount of magnesium ions has no adverse influence on the effect of the present invention.

As the magnesium salts, use may be made of usual ones such as magnesium chloride, sulfate and acetate. Among others, particular preference is given to magnesium acetate.

The concentration of NAC is suitably 0.1~100 mM, preferably 0.5~50 mM and more preferably 1.0~30 mM. The concentration of EDTA is, on the other hand, suitably 0.01~30 mM, preferably 0.5~10 mM.

The concentration of magnesium salts is suitably 0.1~100 mM, more preferably 1~50 mM and most preferably 5~30 mM.

EXAMPLES

In the following, the present invention will be explained with reference to the examples.

Example 1 and Comparison Example 1

Prepared were a reagent group comprising 3 u/m of GluK derived from *Bacillus stearothermophilus* (Glucokinase Code No. 120387 available from Seikagaku Kogyo K.K.), 1 u/ml of G6PDH derived from Leuconostocmesenteroides (available from Oriental Kobo K.K.), 2 mM of ADP.dipotassium salt, 2.5 mM of NADP.sodium salt, 25 mM of glucose, 6 mM of AMP, 10 μm of Ap5A, 25 mM of NAC, 2.5 mM of EDTA and 150 mM of a 0.1% sodium azide in imidazole-acetic acid (buffer solution pH 6.7), and a reagent group comprising 125 mM of CP and 50 mM of magnesium acetate, designated as the first and second reagent groups, respectively. The samples used were dilution runs obtained by diluting about 2000 u/l of CK derived from a rabbit muscle with distilled water.

The dilution runs were measured. The so-called dilution testing wherein the measurements were plotted against the degree of dilution was effected with two reagents, one being an as-prepared reagent and the other being a reagent prepared before 28 days and stored at 4° C. (Example 1).

For the purpose of comparison, testing was carried out under the same conditions as in Ex. 1, except that the first reagent containing 12.5 mM of magnesium sulfate and the second reagent consisting of 125 mM of CP alone were prepared.

To measure the activity of CK, 2.4 ml of each of the first reagents and 20 ul of each sample were filled in a cell having an optical path of 1 cm in length, and the cell was maintained at 37° C. for 3 minutes. To the cell were thereafter added 0.6 ml of each of the second reagents. The acitvity of CK was obtained in terms of changes in absorbance at 340 nm with a spectrophotometer having a cell chamber maintained at 37° C.

Figure 2:
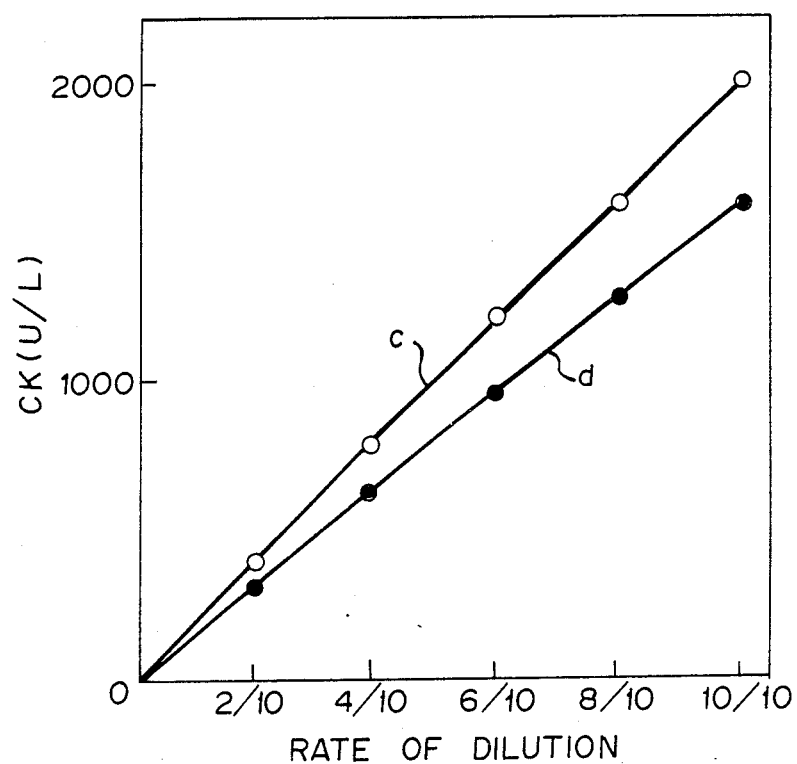
FIG. 2 is a graphical view illustrating the stability of the reagent for comparison.

The results were graphically set forth in FIGS. 1 and 2, from which it is found that the gradient of the calibration curve obtained from the dilution testing does not change at all in Example 1 (FIG. 1 wherein a represents the invented reagent just after preparation, and b represents the invented sample stored for 28 days from preparation), but the calibration curve inclines slowly in Comparison Example 2 (FIG. 2 wherein c represents the comparison reagent just after preparation, and d represents the comparison reagent stored for 28 days from preparation); this clearly indicating a lowering of sensitivity.

Furthermore, in Comparison Example 1, the dilution testing was again carried out, supplementing the reagent degraded during 28-day storage a 4° C. with a fresh one. However, there was no sign of recovery of sensitivity. This suggests that the lowering of sensitivity is clearly caused by the occurrence of the factor inhibiting the activity of CK, not by deteriorations of the reagent.

Reference Example

Prepared were solutions of 25 mM of NAC and 150 mM of imidazole-acetic acid (pH 6.7), to which EDTA and/or magnesium acetate was added to study the influence thereof on the stability of NAC. Each of the aforesaid solution was stored at 37° C., and the quantity of NAC was determined with days, making use of the usual SH group-measuring method.

Figure 3:
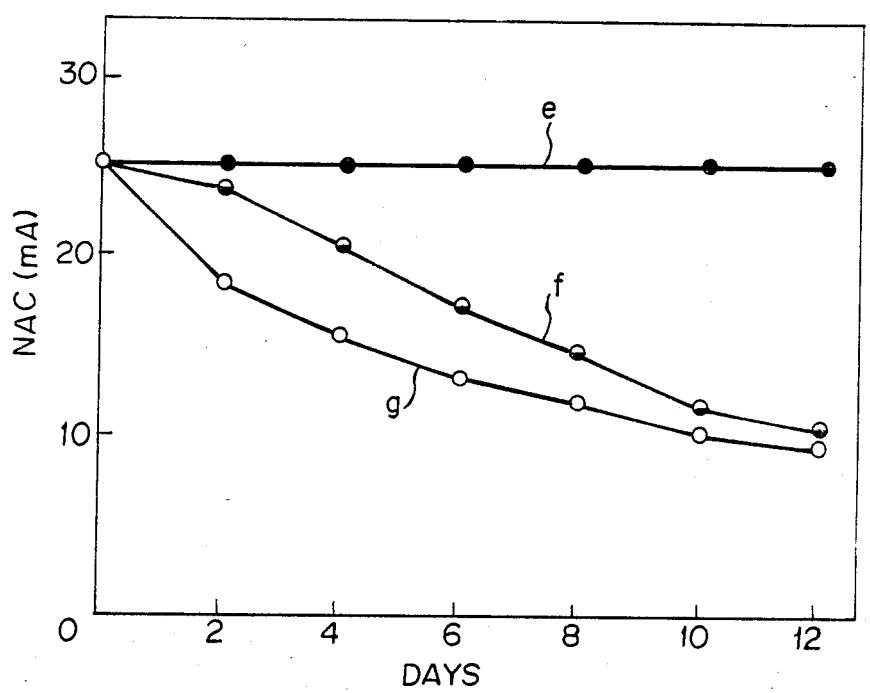
FIG. 3 is a graphical view illustrating effects of coexisting compound(s) on the stability of NAC with lapse of time.

The results are graphically set forth in FIG. 3, from which it is found that EDTA makes some contribution to the stabilization of NAC, but its stabilization effect is further increased in the absence of magnesium acetate. In FIG. 3, e represents the EDTA containing reagent, f represents the reagent containing EDTA and magnesium acetate, and g represents the reagent consisting of NAC alone.

According to the reagents of the present invention for the determination of CK wherein NAC co-exists with EDTA, but is not allowed to co-exist with magnesium salts, it is possible to stabilize NAC, that is an activator for CK, sustain its activation effect over a prolonged period, and suppress the formation of the decomposed product of NAC which inhibits the activity of CK. For those reasons, the invented reagents for the determination of CK can be used over an extended period even in the state of a solution, and can be prepared in larger amounts at a time. This makes it possible to cope rapidly with emergency examinations, and to improve manipulation efficiency and reduce the frequency of the disposal of surplus reagents.

What is claimed is:

1. In a reagent kit for use in the determination of creatine kinase containing creatine phosphate, ADP, glucose, HK or Gluk, NAD(P), G6PDH, magnesium salts, NAC and EDTA as essential components, based on the following reaction formulae 1, 2 and 3, the improvement which comprises having as separate reagents a reagent group containing at least a magnesium salt as the essential components and reagent group containing at least N-acetylcysteine and ethylenediaminetetraacetic acid as essential components, and the magnesium salt being separated from the group of the EDTA and NAC until the determination is carried out:

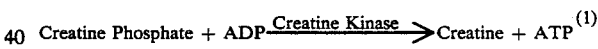

Creatine Phosphate + ADP $\xrightarrow{\text{Creatine Kinase}}$ Creatine + ATP  (1)

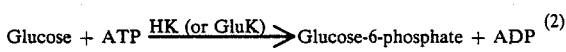

Glucose + ATP $\xrightarrow{\text{HK (or GluK)}}$ Glucose-6-phosphate + ADP  (2)

Glucose-6-phosphate +  (3)

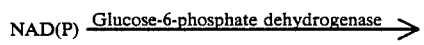

NAD(P) $\xrightarrow{\text{Glucose-6-phosphate dehydrogenase}}$

6-Phosphogluconate + NAD(P)H wherein ADP represents adenosine diphosphate, ATP represents adenosine, triphosphate, HK represents hexokinase, GluK represents glucokinase, NAD(P) represents beta-nicotinamide adenine dinucleotide (phosphate), NAD(P)H represents reduction type beta-nicotinamide adenine dinucleotide (phosphate).

2. A reagent kit of claim 1 wherein the reagent group containing N-acetylcysteine and ethylenediaminetetraacetic acid is composed of ADP, glucose, HK or GluK, glucose-6-phosphate dehydrogenase and NAD(P).

3. A reagent kit of claim 1 wherein the reagent group containing magnesium also contains creatine phosphate.

4. A reagent kit of claim 1 wherein the concentration of N-acetylcysteine is 1~50 mM.

5. A reagent kit of claim 1 wherein the concentration of ethylenediaminetetraacetic acid is 0.5~10 mM.

6. A reagent kit of claim wherein the concentration of magnesium salts is 5~30 mM.

* * * * *

UNITED STATES PATENT AND TRADEMARK OFFICE
CERTIFICATE OF CORRECTION

PATENT NO.   : 4,888,289

DATED        : December 19, 1989

INVENTOR(S)  : Tetuji TAKAMI, Hiroyki TSUBOTA, Hisashi OCHI, Takanari SHIRAISHI, Hitoshi KONDO, Kazuhiko NAGATA, Takaaki MATSUO It is certified that error appears in the above-identified patent and that said Letters Patent is hereby corrected as shown below:

Cover page, Item [75], after "Japan", add the following:

-- Takanari Shiraishi, Hitoshi Kondo, Kazuhiko Nagata, Takaaki Matsuo, all of Kyoto, Japan--

Signed and Sealed this

Seventh Day of January, 1992

Attest:

HARRY F. MANBECK, JR.

Attesting Officer     Commissioner of Patents and Trademarks